United States Patent [19]

Matthews et al.

[11] 4,094,017

[45] June 13, 1978

[54] KNEE JOINT PROSTHESIS WITH PATELLAR-FEMORAL CONTACT

[76] Inventors: Larry Stanford Matthews; Herbert Kaufer; David Ansel Sonstegard, all c/o Howmedica, Inc., 235 E. 42nd St., New York, N.Y. 10017

[21] Appl. No.: 768,952

[22] Filed: Feb. 16, 1977

[51] Int. Cl.² ............................................. A61F 1/24
[52] U.S. Cl. ................................. 3/1.911; 128/92 C
[58] Field of Search ..................... 3/1.911, 1.91, 22; 128/92 C

[56] References Cited

U.S. PATENT DOCUMENTS

| 3,728,742 | 4/1973 | Averill et al. ......................... 3/1.911 |
| 3,806,961 | 4/1974 | Muller ................................ 3/1.91 X |
| 3,816,855 | 6/1924 | Saleh ................................. 3/1.911 |
| 3,868,730 | 4/1975 | Kaufer et al. ........................... 3/1.91 |
| 3,945,053 | 3/1976 | Hillberry et al. ....................... 3/1.911 |
| 3,964,106 | 6/1976 | Hutter, Jr. et al. ..................... 3/1.911 |

OTHER PUBLICATIONS

"A New Patella Prosthesis" by P. Aglietti et al., Clinical Orthopaedics and Related Research, No. 107, Mar.-Apr., 1975, pp. 175-187.
"The Spherocentric Knee" by Larry S. Matthews et al., Clinical Orthopaedics and Related Research, No. 94, Jul.-Aug. 1973, pp. 234-241.

Primary Examiner—Ronald L. Frinks
Attorney, Agent, or Firm—Connolly and Hutz

[57] ABSTRACT

A knee joint prosthesis of the type described in U.S. Pat. No. 3,868,730 has a pair of inwardly sloped radially merging extensions of its condyle runners forming a patella-guiding trough above and between the runners. The extensions merge smoothly into each other at an angle of about 150°. The center of curvature of the base of the trough is about 1.25 inches about a center located a little behind and somewhat above the center of movement of the femoral component. The extension narrows towards its upper portion. The patellar component, which rides in the base of the trough, is made of ultra-high molecular weight polyethylene and has a circular cross section with two bearing surface facets on both sides of a concave arcuate ridge which tracks in the base of the trough, for substantially complete contact between the patellar component and the trough substantially over their full range of movement. The patellar component is retained in a metal holder which has fixation lugs for connecting it under the patella.

10 Claims. 12 Drawing Figures

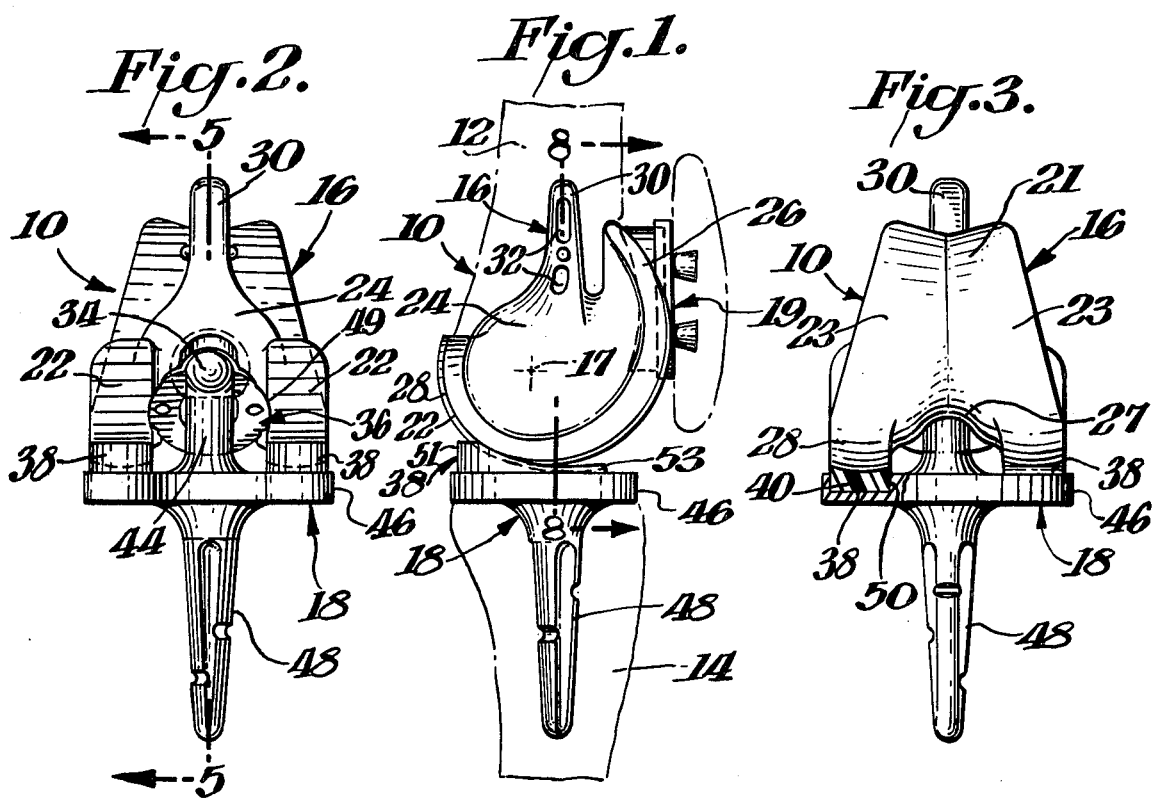
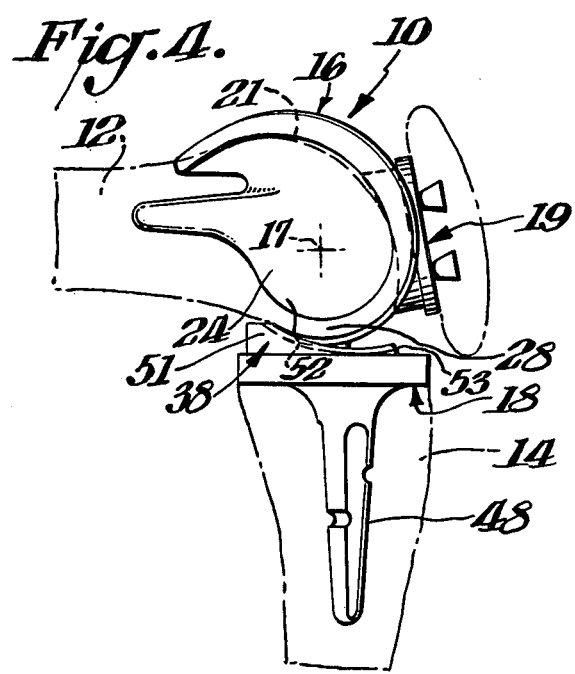

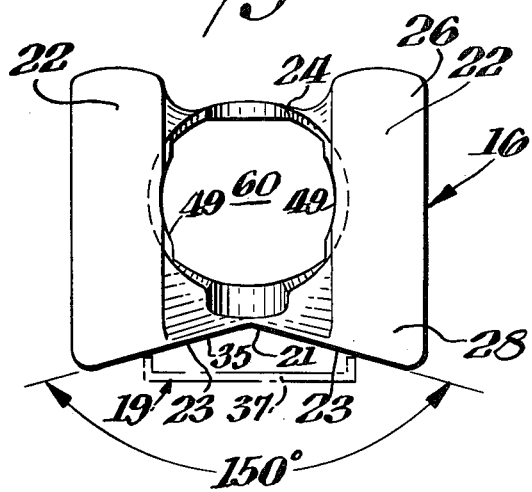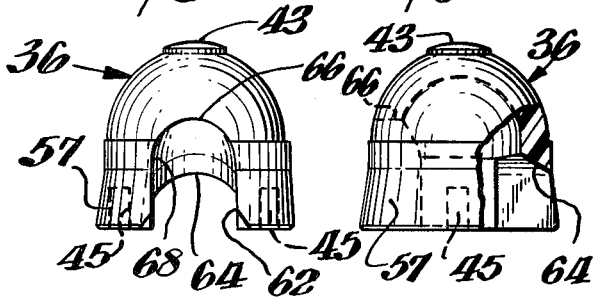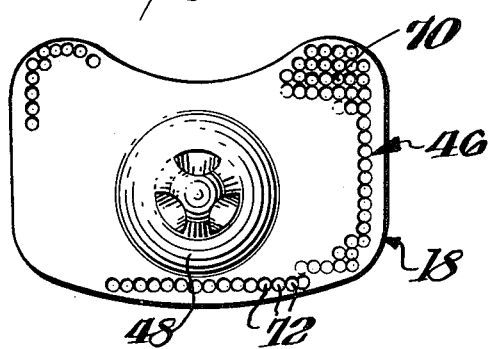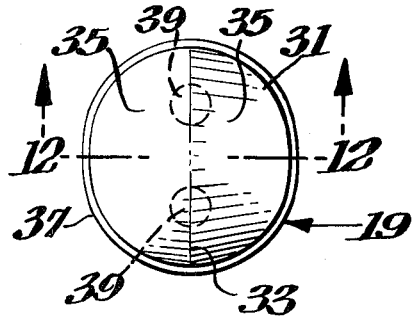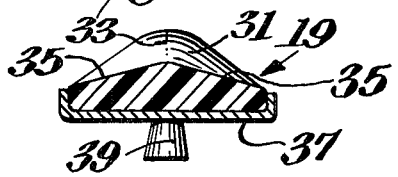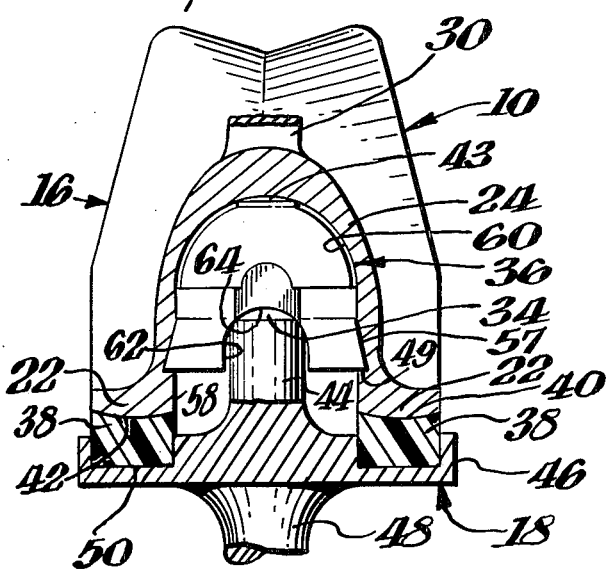

KNEE JOINT PROSTHESIS WITH PATELLAR-FEMORAL CONTACT

BACKGROUND OF THE INVENTION

Many partial knee joint replacement prostheses have proved satisfactory in the treatment of patients with severe tibial femoral knee joint disease. Unfortunately, these prostheses although highly satisfactory for the treatment of patients with arthritis involving the tibial femoral portion of the knee joint do not treat or affect the relationship between the patella and the anterior articular surface of the femur. Patients after knee joint replacement arthrosplasty have frequently continued to complain of patello-femoral joint symptoms — crepitus and pain. This widespread problem of patello-femoral arthritis symptomatic after knee joint arthro plasty has been recognized by many, and attempts have been made to provide prostheses or prosthetic modifications to treat this deficiency. Bechtol, Ewald, and Walker, among others have designed and produced prosthetic components to address this problem. Most of these prostheses rely on provision of an extension of the usual femoral bearing surfaces anteriorly and superiorly on the femur. These replace the femoral portion of the patello-femoral articular bearing surface. A depression or groove is provided in the mid-section of this extension to enhance patellar tracking. The patella, or "knee cap" is customarily resurfaced with an ultra high molecular weight polyethylene inlayed insert. Several years previously the same problem was approached by Doctor McKeever with the production of a metallic resurfacing prosthesis for the articular bearing portion of the patella. It did nothing to replace the diseased portion of the distal femur. More recently, Ewald developed an ultra high molecular weight polyethylene patellar insert, again failing to replace or otherwise substitute for the damaged anterior and superior patello-femoral portions of the femur. The results were unsatisfactory. Total patellectomy, the complete removal of the patella, or "knee cap", has been employed for many years to treat patello-femoral knee joint arthritis. Present efforts toward developing a patello-femoral prosthesis, patello-femoral modifications of present prostheses, and recently reports in the literature document the relatively unsatisfactory effect of total patellectomy.

All presently known designs for prosthetic replacement of patello-femoral joint destruction rely upon a point, or at best a line contact between the patellar bearing surfaces and the femoral bearing surfaces. A very high contact stress between the patella and femur under normal conditions and activities has been documented. This very small area of contact of presently available prostheses, the demonstrated large force magnitudes, and the resulting high bearing surface contact stresses cannot but be detrimental to the satisfactory performance of these prosthetic joints. This is expected to cause accelerated wear on the components and the production of considerable wear debris, which may be damaging to the patient's tissue and may contribute to loosening of the components.

Presently available prosthetic replacements for the patella of ultra high molecular weight polyethylene are cemented using methylmethacrylate into the remaining patellar trabecular bone. Considering the high joint contact stresses, and the high magnitudes of force bearing on these prosthetic knee caps, one would expect elastic and plastic deformations along the compression force lines with a resulting spreading in transverse dimensions of the plastic component. This effect resulting from a Poisson's ratio situation would be expected to generate high shear stress levels at the polyethylene-methacrylate interface and possibly at the methacrylate-bone interface. This could result in loosening.

A single metal resurfacing prosthesis for the patella has not been demonstrated to be of a long term value after considerable numbers of patients have been treated after many years of follow-up. The prosthesis is rarely used today. The ultra high molecular weight polyethylene patellar replacement caused severe wear of the distal femur, subsequent wear of the prothesis, and results in clinical failure.

There is a very significant loss of extension strength with patellectomy. This particularly affects the patients in stair climbing and is also specifically deleterious to the treatment of elderly patients with arthritis. These patients very frequently have extreme weakness of the quadriceps muscles in association with obesity. They cannot tolerate this weakening effect. An object of this invention is to provide a suitable knee replacement prosthesis which overcomes such problems.

SUMMARY

A knee joint prosthesis has a pair of inwardly sloped radially merging extensions of its condyle runners forming a patella-guiding trough above and between the runners. The extensions merge smoothly into each other at an angle of about 150°. The center of curvature of the base of the trough is about 1.25 inches about a center located a little behind and somewhat above the center of movement of the femoral component. The extension narrows towards its upper portion. The patellar component, which rides in the base of the trough, is made of ultra-high molecular weight polyethylene and has a circular cross section with bearing surface facets on both sides of a concave arcuate ridge which tracks in the base of the trough, for substantially complete contact between the patellar component and the trough substantially over their full range of movement. The patellar component is retained in a metal holder which has fixation lugs for connecting it to the patella.

BRIEF DESCRIPTION OF THE DRAWINGS

Novel features and advantages of the present invention will become apparent to one skilled in the art from a reading of the following detailed description in conjunction with the accompanying drawings wherein similar reference characters refer to similar parts and in which:

FIG. 1 is a side view in elevation of a knee prosthesis which is one embodiment of this invention implanted between a femur and tibia, which are shown in phantom outline;

FIG. 2 is a posterior elevational view of the embodiment shown in FIG. 1;

FIG. 3 is an anterior elevational view of the embodiment shown in FIG. 1;

FIG. 4 is a side elevational view of the embodiment shown in FIG. 1 with the knee joint flexed in the sitting position;

FIG. 5 is an enlarged full size cross sectional view taken through FIG. 2 along the line 5—5;

FIG. 6 is a full size bottom plan view of the femoral component shown in FIGS. 1-5;

FIG. 7 is a full size bottom plan view in elevation of the tibial component of the embodiment shown in FIGS. 1-5;

FIG. 8 is a cross sectional view taken through FIG. 1 along the line 8—8;

FIG. 9 is an outside view in elevation of the anterior portion of the plastic socket interposed between the femoral and tibial component shown in FIGS. 1-5;

FIG. 10 is a side view in elevation partly broken away in cross section of the plastic socket shown in FIG. 9;

FIG. 11 is a posterior view in elevation of the patellar component shown in FIGS. 1-5; and FIG. 12 is a cross sectional view taken through FIG. 11 along the line 12—12.

DESCRIPTION OF THE PREFERRED EMBODIMENT

In FIGS. 1-3 and 5 is shown a knee joint prosthesis 10 in the extended and in the partially flexed positions, respectively in which the upper and lower portions of the leg represented by femur 12 and tibia 14 are in anatomical alignment with each other. Joint 10 includes a femoral component 16 and a tibial component 18 coupled by ball and socket connection 20 and a contacting patellar component 19 (later described in detail). Femoral component 16 has a pair of spaced substantially parallel spheroidally curved condyle runners 22 straddling a hollow central housing 24.

The portions similar to those in U.S. Pat. No. 3,868,730 are further described. Condyle runners 22 each have a front lower portion 26 having a relatively larger radius of curvature and a rear upper portion 28 having a relatively smaller radius portion. The radius of curvature of front lower portion 26 is, for example, twice as large as the radius of curvature of rear upper portion 28. Femoral attaching stem 30 is attached to the top of hollow central housing 24 and is substantially of square cross-section with slight lateral depressions 32 in each of the sides for facilitating cementing and retention in the femur.

Ball and socket connection 20 in hollow housing 24 includes spherical ball 34 entrapped within plastic socket 36, later described in detail. Socket 36 is suitably made of ultra high molecular weight polymer such as ultra high molecular weight polyethylene. All other portions of knee joint 10 are made of a strong non-corrosive metal having stable expansion and other biocompatible physical characteristics, with the exception of shoes 38 which are also made of ultra high molecular weight polyethylene. The metal portions are advantageously made of metal compatible with the human body such as Vitallium, the trademark of Howmedica Inc. for a cobalt-chromium alloy, developed and used for cast partial and full dentures, and for internal applications by surgeons. When polished, it is exceedingly smooth and permanently lustrous. Its outstanding qualities are permanent inertness in relation to living tissues, and high resistance to corrosion. Vitallium has for example the following composition:

Cobalt and chromium constitute over 90% of its composition. Sp. gr. 8.29; tensile strength, 100,000–120,000 lb./sq. in.: yield point, 70,000–80,000 lb./sq. in.: Rockwell "C" hardness, 23–28; elongation, 15–20% modulus of elasticity in tension, 30,000,000–32,000,000.

Condyle runners 22 correspond to the condyle portions of a human knee joint and also have a transverse radius of curvature shown in FIG. 3 to make their surfaces substantially spheroidial. Transverse radius of curvature 40 shown in FIG. 3 is preferably substantially equal to the smaller radius of curvature of condyle runner upper rear portions 28.

Shoes 38 shown in FIG. 5 correspond to the plateau portions of the human knee and have a concave surface 42 shown in FIG. 8, which substantially correspond to the shape of lower condyle runner portions 26 to cause these portions to intimately nest with each other in the extended position shown in FIG. 1 and provide firm support for the extended leg. Shoes 38 have substantially the same transverse radius as curvature 40 shown in FIG. 3. This geometry helps provide the aforementioned stable nesting in the extended position, and provides an interference control of the rotation and wobbling movement facilitated by the ball 34 and socket 36. The posterior portions 51 of shoes 38 are higher than the anterior portions 53 to provide limits of travel for the condyle runners in both directions as illustrated in FIGS. 1 and 4.

Ball 34 is disposed on the top of connecting rod 44, which is mounted on the top of base 46 of tibial component 18. A regularly gouged tibial connecting stem 48 extends downwardly into tibia 14 from the bottom of base 46. Shoes 38 are mounted in recesses 50 in the upper surface of base 46.

FIG. 4 shows the position of joint 10 when femoral component 16 is rotated to a horizontal position, such as when a person is in the sitting position. This engages the upper rear portions 28 of condyle runners 22 with shoes 38. The flexure motion is smoothly arrested by an outward protrusion or slight thickening of the terminal ends 52 of upper rear condyle portions 28 which wedge against the rear ends of shoes 38. This smoothly arrests the flexure movement without any clunking and simulates the normal knee action.

The extending movement of joint 10 about axis 56 of ball and socket joint 20 is arrested by the nesting of lower larger radius of curvature portions 26 of condyle runners 22 within shoes 38. Smaller radius of curvature condyle portions 28 have a coaxial axis of rotation with ball center 56 in the position shown in FIG. 5. This causes the larger radius of curvature condyle runner portions 26 to firmly engage into the concave surfaces 42 within shoes 38 and thus provide secure abutment and firm support for each other. During the approximate 120° movement of joint 10 from the extended position shown in FIG. 1 to the flexed position shown in FIG. 4 through intermediate position 5, smaller radius of curvature portions 28 of condyle runners 22 move slightly free of internal shoe surfaces 42 which thus allows a light wobbling or controlled play within the confines of shoes 38 until the bottoms of condyle runners 22 engage the outer edges 58 of shoes 38 which limit such movement. This simulates the normal rotational inward and outward tilting or wobbling of a normal knee joint throughout the flexed position and with more restraint in the extended position.

FIGS. 7-10 show the manner in which plastic insert 36 is disposed about ball 34 and inserted within cavity 60 in hollow central housing 24. Connecting rod 44 is narrower than the width of slots 62 and 68 to insure non-interference with the play or wobbling action throughout the flexed orientation of knee joint 10.

FIG. 7 shows the bottom surface 70 of tibial base 46 serrated by spherical pits 72, which help cement base 46 to tibia 14.

FIGS. 1-5 also show the principal features of this invention including patellar component 19 which rides or tracks in the shallow right circular trough 21 formed between a merging pair of broadly inclined extensions 23 of condyle runners 22. Inclined extensions 23 are disposed relative to each other at an approximate angle of about 150° with a smooth trough 21 having a substantially right circular arcuate configuration as shown in FIG. 1. The center of curvature 25 of trough is a little behind and somewhat above the center of rotation 17 of ball and socket connection 20. The radius of curvature of arcuate trough base 21 is about 1.25 inches (31.8 mm) and its center of curvature 25 is for example 0.156 inch (3.96 mm), behind and 0.625 inch (15.88 mm) above center of rotation 17.

Inclined extensions 23 are substantially straight in the lateral direction but may also have a slight curvature which increases from base of the trough to the outer lateral regions. The merging extensions narrow in width from bottom toward the top and have smoothly rounded corners and junctions. The bottom portion of extensions 23 end in a U-shaped terminal portion 27 disposed between condyle runners 22 on both sides of the relative path of movement of connecting rod 44 which supports ball 34.

Details of patellar component 19 are shown in FIGS. 11 and 12 as well as FIGS. 1 and 4. The bearing portion 31 is made of ultra-high molecular weight polyethylene to bear smoothly against the metal extensions 23 and trough 21 between them. FIGS. 4 and 11 shows concave arcuate ridge 33 between the concave bearing facets 35. Ridge 33 is a concave right circular arc of a circle which closely matches the circular trough 21 between extensions 23. Facets 35 are substantially concave or they may be of any shape required to make them match the outwardly flairing extensions 23. When extension 23 are outwardly curved, facets 35 may be slightly concave to match them. Bearing portion 31 is held within a metal retainer or cup 37 of circular configuration to contain the circular plan shape of patellar component 19. Metal retainer 37 provides strong rigid support for bearing portion 31 and has a pair of patella-attaching lugs 39 on its outer surface. FIG. 1 shows lugs 39 implanted in a schematic representation of the patellar knee cap illustrated in broken line.

FIGS. 8, 9 and 10 show plastic socket 36 interposed between spherical ball 34 and hollow cavity 60 in femoral component 16. The posterior portion of socket 36 has a slot 62 having a relatively lower outer dome 64 relative to high outer dome 66 of slot 68 in the anterior portion of socket 36. This provides for the relative angular movement of connecting rod 44 which is narrower than the width of slots 62 and 68. A button 43 is disposed on the top of socket 36 and a pair of flexing pits 45 are provided in the flaired skirt 57 of socket 36 to provide a means of locking and unlocking them over shoulder 49 in hollow cavity 60 as shown in FIG. 8.

The development of a geometric radius of curvature for the femoral component of a patello-femoral prosthesis or of a patello-femoral modification of a tibial-femoral prosthesis and the production of a patellar bearing surface which substantially matches these radii of curvature for all positions of knee flexion to near full knee extension, provides for total contact of the ultra high molecular weight polyethylene plastic replacement components against the patello-femoral bearing surface of the prosthetic femoral component. The joint contact stress is thus much reduced and the expected wear, wear particle, and deformation of components would be minimized during normal implanted function.

The 150° trench or groove provides accurate tracking of the prosthetic patellar component vertically in alignment approximate to the femoral shaft. This provides stable function even in the face of moderate asymmetric muscle dysfunction.

The containment of the ultra high molecular weight polyethylene patellar component within metal decreases the possibility of significant deformations of the plastic component and minimizes shear effects. It decreases the possibility of implanted loosening and failure.

This invention provides no metal to metal contact which minimizes wear and production of irritating wear particles.

All bearing surfaces of the invention are of plastic on polished metal for low friction and durability.

It is anticipated that this invention will first be made proportionate with the present regular sized Spherocentric Knee (U.S. Pat. No. 3,868,730) joint replacement prosthesis. A smaller version is planned in the future. It would be anticipated that a smaller version of the patello-femoral modification would be designed and produced to match the smaller unmodified knee.

Similar proportionate dimensional adjustments are to be utilized in the design of patello-femoral prostheses and modifications of other tibial-femoral knee joint replacement prostheses.

Although present plans do not call for any "right-sided" or "left-sided" differentiation, this may prove to be necessary. In this case, the line representing the depth of the notch or trench would be angled with the superior most portion of the trench slightly lateral to its present position. This is not anticipated to be necessary. The patello-femoral aspects of the prosthesis described herein can be used by itself without attachment to any particular tibial-femoral prosthesis if isolated patello-femoral arthritis occurs.

The new features of this invention are as follows:

1. The production of patello-femoral resurfacing flares centered about an axis and having a defined angle of intersection between flares;

2. The complete mating of the total contact surface between the ultra high molecular weight polyethylene plastic patellar components and the polished metal femoral component using the described radii of curvature and notch angles of intersection.

3. The containment of the plastic resurfacing portion of the prosthetic modifications in metal to prevent deformation and loosening.

We claim:

1. A knee joint prosthesis comprising a femoral component, a tibial component, coupling means connecting said femoral and tibial components for movement relative to each other, said coupling means including a pair of spaced substantially spherically curved condyle runners, a femoral attaching means in the top of the femoral component, the tibial component having a base, tibial connecting means on the bottom of the base, the coupling means also including a pair of spheriodally curved spaced parallel concave shoes on the base having upper surfaces intimately mating with the condyle runners for smooth relatively sliding movement between them, a pair of broadly inclined and smoothly merging anterior and superior extensions of the condyle runners on the femoral component, the extensions smoothly merging with each other to form a substantially circular arcuate trough disposed midbetween and parallel to the condyl runners, the trough having a center of curvature slightly posterior and somewhat superior to the center of movement of the femoral component relative to the tibial component, a patellar component, the posterior portion of the patellar component having a concave arcuate ridge for substantially matching the circular trough, the patellar component having a pair of bearing facets on both sides of the ridge which substantially match the lateral sides of the extensions whereby substantially total contact is maintained between the ridge and facets on the patellar component and the trough substantially throughout the entire range of movement of the prosthesis, the femoral and tibial components being made of a biocompatible metal, the bearing facets and ridge of the patellar component being made of a very strong and wear-resistant plastic material, and patellar attaching lugs on the anterior of the patellar component for connecting it to the patella.

2. A prosthesis as set forth in claim 1 wherein the extensions are disposed at an angle of about 150° relative to each other.

3. A prosthesis as set forth in claim 2 wherein the extensions are substantially flat in the lateral direction.

4. A prosthesis as set forth in claim 3 wherein the overall width of the extensions narrows in the superior direction.

5. A prosthesis as set forth in claim 4 wherein a lower terminal portion of the flaired extension is disposed between a portion of the condyle runners.

6. A prosthesis as set forth in claim 1 wherein the bearing facets of the patellar component is held within a metal retainer, and patella attaching lugs are disposed on the anterior portion of the metal retainer.

7. A prosthesis as set forth in claim 1 wherein the coupling means between the femoral and tibila components includes a ball and socket joint.

8. A prosthesis as set forth in claim 7 wherein the ball and socket joint includes a cavity in the bottom of the femoral component, a plastic socket liner in the cavity, a ball connected to an upper portion of the tibial component, and the ball is spherically engaged within the socket liner.

9. A prosthesis as set forth in claim 1 wherein a central vertical section connects the posterior of the extensions to the femoral component.

10. A prosthesis as set forth in claim 1 wherein the patellar component is circular in cross section, has a central concave arcuate ridge and bearing facets on both sides of the ridge.

* * * * *